US010092767B1

(12) United States Patent
Newton et al.

(10) Patent No.: US 10,092,767 B1
(45) Date of Patent: Oct. 9, 2018

(54) SYSTEM AND METHOD FOR NETWORK-ENABLED AUTOMATIC ELECTRONIC DEFIBRILLATORS (71) Applicant: CARDIOSPARK LLC, Tucson, AZ (US)

(72) Inventors: Carter Newton, Tucson, AZ (US); Thomas P. Colberg, Tucson, AZ (US); Norman P. Soloway, Tucson, AZ (US)

(73) Assignee: CARDIOSPARK LLC, Tucson, AZ (US)

(*) Notice: Subject to any disclaimer, the term of this patent is extended or adjusted under 35 U.S.C. 154(b) by 0 days.

(21) Appl. No.: 15/674,390

(22) Filed: Aug. 10, 2017

Related U.S. Application Data (60) Provisional application No. 62/504,993, filed on May 11, 2017, provisional application No. 62/373,800, filed on Aug. 11, 2016.

(51) Int. Cl.
A61B 90/98 (2016.01)
A61N 1/39 (2006.01)
H04L 29/08 (2006.01)
G08B 21/04 (2006.01)
G08B 27/00 (2006.01)

(52) U.S. Cl.
CPC ............ A61N 1/3904 (2017.08); A61B 90/98 (2016.02); G08B 21/0446 (2013.01); G08B 21/0492 (2013.01); G08B 27/001 (2013.01); H04L 67/12 (2013.01)

(58) Field of Classification Search
CPC ............................ G08B 27/001; A61B 90/98
See application file for complete search history.

(56) References Cited

U.S. PATENT DOCUMENTS

| 5,593,426 A * | 1/1997 | Morgan ............... A61N 1/39 128/903 |
| 5,645,522 A | 7/1997 | Lurie et al. ............ 601/43 |
| 7,657,311 B2 | 2/2010 | Bardy et al. ............ 607/2 |
| 7,672,720 B2 | 3/2010 | Heath ................ 607/5 |
| 8,050,759 B2 | 11/2011 | Stegemann et al. ......... 607/17 |
| 8,078,288 B2 | 12/2011 | Heath ............... 607/142 |
| 8,260,413 B2 | 9/2012 | Heath .............. 607/5 |
| 8,301,232 B2 | 10/2012 | Albert et al. ........... 600/509 |

(Continued)

FOREIGN PATENT DOCUMENTS

JP 2011032640 A * 2/2011 ........... E05B 49/00

OTHER PUBLICATIONS

Notice of Allowance issued in corresponding U.S. Appl. No. 15/661,398, dated May 15, 2018, 10 pgs.

(Continued)

Primary Examiner — Tammie K Marlen
(74) Attorney, Agent, or Firm — Hayes Soloway P.C.

(57) ABSTRACT

A system and method of network-enabled automatic electronic defibrillators (AEDs) may be used to assist with cardiac emergencies. The system includes at least two AEDs positioned in different geographic locations. At least one location-providing tag is positioned on each of the at least two AEDs. A controller is capable of communicating with the location-providing tag of each of the at least two AEDs through at least one network connection. When a cardiac emergency occurs, an AED located nearby may be identified or requested to assist with the emergency.

10 Claims, 7 Drawing Sheets

(56) References Cited

U.S. PATENT DOCUMENTS

| | | | |
|---|---|---|---|
| 8,509,882 B2 | 8/2013 | Albert et al. | 600/509 |
| 8,615,295 B2 | 12/2013 | Savage et al. | 607/5 |
| 8,700,137 B2 | 4/2014 | Albert | 600/513 |
| 8,781,576 B2 | 7/2014 | Savage et al. | 607/5 |
| 9,026,202 B2 | 5/2015 | Albert | A61B 5/0404 |
| 9,101,778 B2 | 8/2015 | Savage et al. | A61N 1/3918 |
| 2003/0149423 A1 | 8/2003 | Fischell | 604/892.1 |
| 2005/0143776 A1 | 6/2005 | Brown | A61N 1/18 |
| 2006/0173498 A1 | 8/2006 | Banville et al. | A61N 1/39 |
| 2007/0218869 A1* | 9/2007 | Thijs | G08B 25/016 455/404.2 |
| 2010/0030290 A1 | 2/2010 | Bonner et al. | 607/5 |
| 2010/0241181 A1 | 9/2010 | Savage et al. | 607/5 |
| 2014/0005736 A1 | 1/2014 | Geheb | 607/7 |
| 2014/0039593 A1 | 2/2014 | Savage et al. | A61N 1/046 |
| 2014/0039594 A1 | 2/2014 | Savage et al. | A61N 1/046 |
| 2014/0323923 A1 | 10/2014 | Khuon et al. | 600/595 |
| 2014/0324111 A1 | 10/2014 | Wu | 607/7 |
| 2015/0217121 A1 | 8/2015 | Subramanian et al. | A61N 1/39 |
| 2016/0038751 A1 | 2/2016 | Broder et al. | A61N 1/39 |
| 2016/0328950 A1* | 11/2016 | Pelletier | G08B 7/066 |

OTHER PUBLICATIONS

Official Action issued in corresponding U.S. Appl. No. 15/661,398, dated Dec. 12, 2017, 30 pgs.

"www.alivecor.com" AliveCor company website for Kardia Mobile, personal EKG. Printed Aug. 9, 2017 (9 pages).

International Preliminary Report on Patentability issued in application No. PCT/US2016/023295, dated Sep. 28, 2017 (7 pgs).

* cited by examiner

```
A geographic location of a plurality of AEDs is identified
using at least one geographic-locating tag connected to         —— 102
each of the plurality of AEDs, respectively.
```

```
The plurality of AEDs are communicatively connected to
a controller using the at least one geographic-locating tag     —— 104
and at least one network.
```

```
At least one of the plurality of AEDs is located in
response to the cardiac emergency, wherein the at least
one of the plurality of AEDs is positioned near a location      —— 106
of the cardiac emergency.
```

SYSTEM AND METHOD FOR NETWORK-ENABLED AUTOMATIC ELECTRONIC DEFIBRILLATORS

CROSS REFERENCE TO RELATED APPLICATION

This application claims priority from U.S. Provisional application Ser. No. 62/373,800, filed Aug. 11, 2016 and from U.S. Provisional application Ser. No. 62/504,993, filed May 11, 2017, the contents of which are incorporated herein by reference.

FIELD OF THE DISCLOSURE

The present disclosure is generally related to medical devices and more particularly to a system and method for network-enabled automatic electronic defibrillators (AEDs).

BACKGROUND OF THE DISCLOSURE

Sudden cardiac arrest (SCA), which is also known as Sudden Cardiac Death (SCD), is a leading cause of death among adults over the age of 40 in the U.S., and throughout the world. In the U.S. alone, more than 300,000 men and women of all ages experience SCA annually. Tragically, nearly nine out of 10 victims die. In relation to other common lethal conditions, the number of people who die in the US each year from SCA is roughly equivalent to the number of people who die from Alzheimer's disease, assault with firearms, breast cancer, cervical cancer, colorectal cancer, diabetes, HIV, house fires, motor vehicle accidents, prostate cancer and suicides combined. Accordingly, it is evident that SCA is a costly and disruptive medical affliction on our society.

A paramount of medicine is the fact that the steady circulation of blood is crucial to the proper functioning of the human body. The circulation of blood is governed by the heart, whose expansion and contraction is in turn controlled by a regular pattern of electrical impulses. When this pattern of electrical impulses becomes chaotic or overly rapid, SCA may take place. Tragically, the victim typically collapses and dies unless he or she receives proper medical attention. The most successful therapy for sudden cardiac arrest is prompt and appropriate defibrillation. A defibrillator uses electrical shocks to restore the proper functioning of the heart. A crucial component of the success or failure of defibrillation, however, is time. Ideally, a victim should be defibrillated immediately upon suffering a sudden cardiac arrest, as the victim's chances of survival dwindle rapidly for every minute without treatment. In fact, research has determined that the full survival of an out-of-hospital cardiac death is 5-7%, where full survival is understood as normal brain and heart function, and this statistic has not changed significantly in the past 15 years.

While defibrillators are commonplace within medical facilities, automated external defibrillators (AEDs) are increasingly being installed in public places. AEDs are typically located in emergency response vehicles, medical facilities, and many public buildings. Efforts have been made to improve the availability of AEDs, so that they are more likely to be in the vicinity of sudden cardiac arrest victims. Also, advances in medical technology have reduced the cost and size of AEDs. Some modern AEDs approximate the size of a laptop computer or backpack. Even small devices may typically weigh 10 pounds or more. Accordingly, they are increasingly found in public facilities (e.g., airports, schools, gyms, etc.).

Currently available AEDs, while effective, are still less than ideal for most situations. For example, while AEDs are readily available in public settings and are not complicated to use, it has been found that untrained bystanders typically cannot, or will not, utilize devices even when they are easily accessible. Even when one does attempt to utilize an AED in a public setting, it can be a challenge to actually locate an AED. Specifically, when a person suffers from SCA in an airport or public building in which multiple AEDs have been distributed, the victim's companion or a stranger would have to locate and run towards the nearest AED, pull the device off the wall, and return to the collapsed victim to render assistance. During that time, precious minutes may have passed. According to some estimates, the chance of surviving a sudden cardiac arrest is 90% if the victim is defibrillated within one minute, but that chance declines by 10% for every minute thereafter. A defibrillator design that reduces the time to defibrillation by even two to three minutes will save more lives.

Despite the increasing presence of AEDs in public places, a central problem with combating SCA still remains: approximately 80% of sudden cardiac arrests occur at a private home or residence, not at a public building. Until AEDs are readily available for use in generally private places, such as homes and in cars, their effectiveness will remain significantly limited. More specifically, until AEDs are designed to be conveniently and regularly carried by non-professional rescuers, and are designed for quick, uncomplicated use, the effectiveness of AEDs may remain limited.

Thus, there exists a need to make AEDs accessible such that they can be widely used in home settings by untrained, first-time users.

SUMMARY OF THE DISCLOSURE

Embodiments of the present disclosure provide a system and method of network-enabled automatic electronic defibrillators. Briefly described, in architecture, one embodiment of the system, among others, can be implemented as follows. At least two AEDs are positioned in different geographic locations. At least one location-providing tag is positioned on each of the at least two AEDs. A controller is capable of communicating with the location-providing tag of each of the at least two AEDs through at least one network connection.

In such embodiment, the system may be characterized by one or more of the following features:
  (a) where the at least one location-providing tag further comprises at least one of: a RFID chip, a GPS chip, and a NFC chip;
  (b) where the at least one network connection further comprises at least one of: a wireless network, a hardwired network, a WiFi network, and a Bluetooth network;
  (c) where the at least one location-providing tag provides a location of one of the at least two AEDs based on a network identification through which the at least one location-providing tag communicates with the controller;
  (d) where the network identification further comprises at least one of: a MAC address, an identifier string, a WiFi network ID, and a cellular network;

(c) where the controller further comprises a display having a map, wherein at least a portion of the at least two AEDs are displayable on the map;
(f) where the controller is capable of communicating with a human individual associated with at least one of the at least two AEDs with an electronic message;
(g) where the electronic message is a text message transmitted to portable electronic communication device of the human individual requesting use of the associated at least one AED to the human individual;
(h) where communication between the controller and the location-providing tag of each of the at least two AEDs further comprises at least one of: a status ping transmitted at predetermined intervals, wherein the status ping identifies at least one of a functioning state and geographic location of the at least two AEDs; a changed location status ping communicated when a geographic location of the at least two AEDs is changed; an alert message communicating a notification of a medical emergency to a human individual associated with one or more of the at least two AEDs; and an alert message communicating a notification of a medical emergency to a medical care provider;
(i) where the at least one location-providing tag is in communication with a wearable health sensor, wherein data of the wearable health sensor is communicated to the controller when the data identifies an abnormal medical emergency; and
(j) where at least a portion of the at least two AEDs is mobile.

The present disclosure can also be viewed as providing methods of locating an automatic electronic defibrillator (AED) for use in a cardiac emergency. In this regard, one embodiment of such a method, among others, can be broadly summarized by the following steps: identifying a geographic location of a plurality of AEDs using at least one geographic-locating tag connected to each of the plurality of AEDs, respectively; communicatively connecting the plurality of AEDs to a controller using the at least one geographic-locating tag and at least one network; and locating at least one of the plurality of AEDs in response to the cardiac emergency, wherein the at least one of the plurality of AEDs is positioned near a location of the cardiac emergency.

In such embodiment, the method may be characterized by one or more of the following features and/or steps:
(a) where the at least one geographic-locating tag further comprises at least one of: a RFID chip, a GPS chip, and a NFC chip;
(b) where the at least one network connection further comprises at least one of: a wireless network, a hardwired network, a WiFi network, and a Bluetooth network;
(c) identifying the geographic location of the plurality of AEDs based on a network identification of the network, wherein the network identification further comprises at least one of: a MAC address, an identifier string, a WiFi network ID, and a cellular network;
(d) using a graphical display having a map, wherein the identified geographic location of at least a portion of the plurality of AEDs is displayable on the map;
(e) communicating with a human individual associated with at least one of the plurality of AEDs with a text message transmitted to portable electronic communication device of the human individual; and
(f) communicating between the controller and the location-providing tag of each of the plurality of AEDs by: transmitting a status ping at predetermined intervals, wherein the status ping identifies at least one of a functioning state and geographic location of the plurality of AEDs; transmitting a changed location status ping when a geographic location of the plurality of AEDs is changed; transmitting an alert message having a notification of a medical emergency to a human individual associated with one or more of the plurality of AEDs; and transmitting an alert message having a notification of a medical emergency to a medical care provider.

Embodiments of the present disclosure also provide a network-enabled first aid system. Briefly described, in architecture, one embodiment of the system, among others, can be implemented as follows. A plurality of first aid kits each have an automatic electronic defibrillator (AED) and each connected to a control station using communication networks. A message is transmitted from the control station to at least a portion of the plurality of first aid kits, wherein the message requests use of the AED within the portion of the plurality of first aid kits, wherein in response to the message, one of the plurality of first aid kits is transported to a location of a cardiac emergency.

In yet another embodiment of the disclosure, a plurality of AEDs are located within a residential community, typically in homes of trained volunteers who agree to monitor the AED readiness, e.g. periodically check battery, and upon notification of a cardiac emergency in their area, if in the neighborhood, rush their AED to assist a victim until an EMS team arrives. Notification of a cardiac emergency is communicated to the volunteers electronically, either through a dedicated alert system, or via telephone. In such cases, a call placed to 911 would trigger a message to send an available EMS team to the victim, and simultaneously or sequentially send messages to the volunteers in the neighborhood. The messages the volunteer receive will include the address of the emergency. In many cases, due to their physical proximity to the victim, the volunteers may be expected to arrive to the victim before the EMS team, so that the volunteers may begin providing timely AED support until the EMS team arrives.

In yet another alternative embodiment, AEDs also may be located in neighborhoods in public locations. In order to protect the AEDs the AEDs preferably are held in lock boxes which automatically unlock when an electronic signal is sent simultaneously or sequentially with notices to volunteers and the EMS team. The lock boxes then may remain unlocked for a short period of time, for example, 5 to 8 minutes to permit volunteer to access the AED, and bring it to the victim. If an AED is removed, the lock box may be programmed to remain unlocked until the AED is returned, whereupon the lock box may automatically relock, e.g. by sensing the presence of the barcode on the AED case when the AED is returned to the lock box. Alternatively, the lock box may be triggered to relock either by remote control, or by the person returning the AED to the lockbox. In a preferred embodiment, the lock box also may include solar cells for maintaining a charge on the AED battery and/or communication equipment and also to power the lock, and/or to power heating and/or cooling devices for maintaining the interior of the lock box and the contained AED at optimal operating temperature.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

To improve upon the survivability of SCA in a home setting or another non-medical setting, a system of network-enabled AEDs is envisioned to allow access to a nearby AED during the event of a cardiac emergency. By knowing the location of existing AEDs in a given geographical region, and organizing the ability to communicate with others to gain access to an AED when a cardiac emergency occurs, the survivability of SCA can be greatly improved. One goal of the subject disclosure is to find a way to make AEDs available in as many locations as possible, which is where they are needed most, and enable consumers to use them with confidence. This can be accomplished by creating a "safe home architecture" that requires collaboration by a partnership of existing manufacturers; services that provide broadband entertainment, security, and medical monitoring services to millions of residences; cell phone networks; smartphone application developers; emergency service providers; and consumers and their families and friends.

Figure 1:
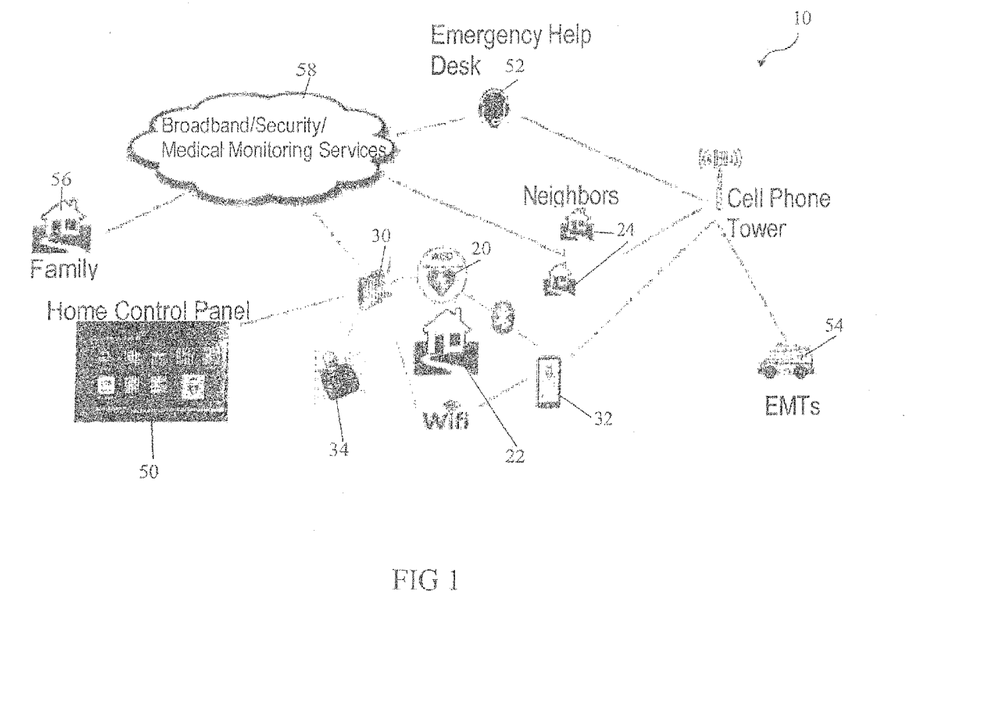
FIG. 1 is a diagrammatical illustration of view illustration of a system of network-enabled automatic electronic defibrillators, in accordance with a first exemplary embodiment of the present disclosure.

FIG. 1 is a diagrammatical illustration of a system of network-enabled automatic electronic defibrillators 10, in accordance with a first exemplary embodiment of the present disclosure. Specifically, FIG. 1 illustrates an example of the "safe home architecture" where an AED 20 located in a home 22 or another non-medical setting can be available to users in the area, such as to neighbors 24. As shown, the AED 20 may be in communication with various devices, such as cellular telephones 32 and landline telephones 34, which in turn may be in communication with a controller 50.

The communication between the devices and the controller 50 may be enabled by networks using known communication protocols, such as WiFi and/or Bluetooth, which may utilize hardware such as routers 30. All of these components and networks together allow for the AED 20 to be capable of communication with the controller 50 and with third parties, such as an emergency help desk 52, Emergency Medical Services 54, and family members 56 of a patient, all of which may be able to receive communications through a monitoring service 58.

In use, when a cardiac emergency occurs, the system 10 is capable of identifying the location of an AED 20 which is closest or most accessible to the patient suffering from the cardiac emergency. For example, upon notification of the cardiac emergency, the controller 50 may be used to quickly identify the location of nearby AEDs 20, for example, by displaying the locations on a map of a display or GUI within the controller. Electronic messages may be sent to the AEDs 20 which are closest or most accessible to the patient. The electronic messages may be transmitted through the various communication networks and to the AED 20 itself, or to communication devices (cellular phones 32, landline phone 34, etc.) carried or accessible to nearby people who could assist with bringing an AED to the location of the patient in need. Accordingly, the system 10 may be founded on an already installed base of AEDs 20 and future AEDs by connecting all AEDs 20 within the community, creating an environment connecting neighbors in need with neighbors who have AEDs.

Figure 2:
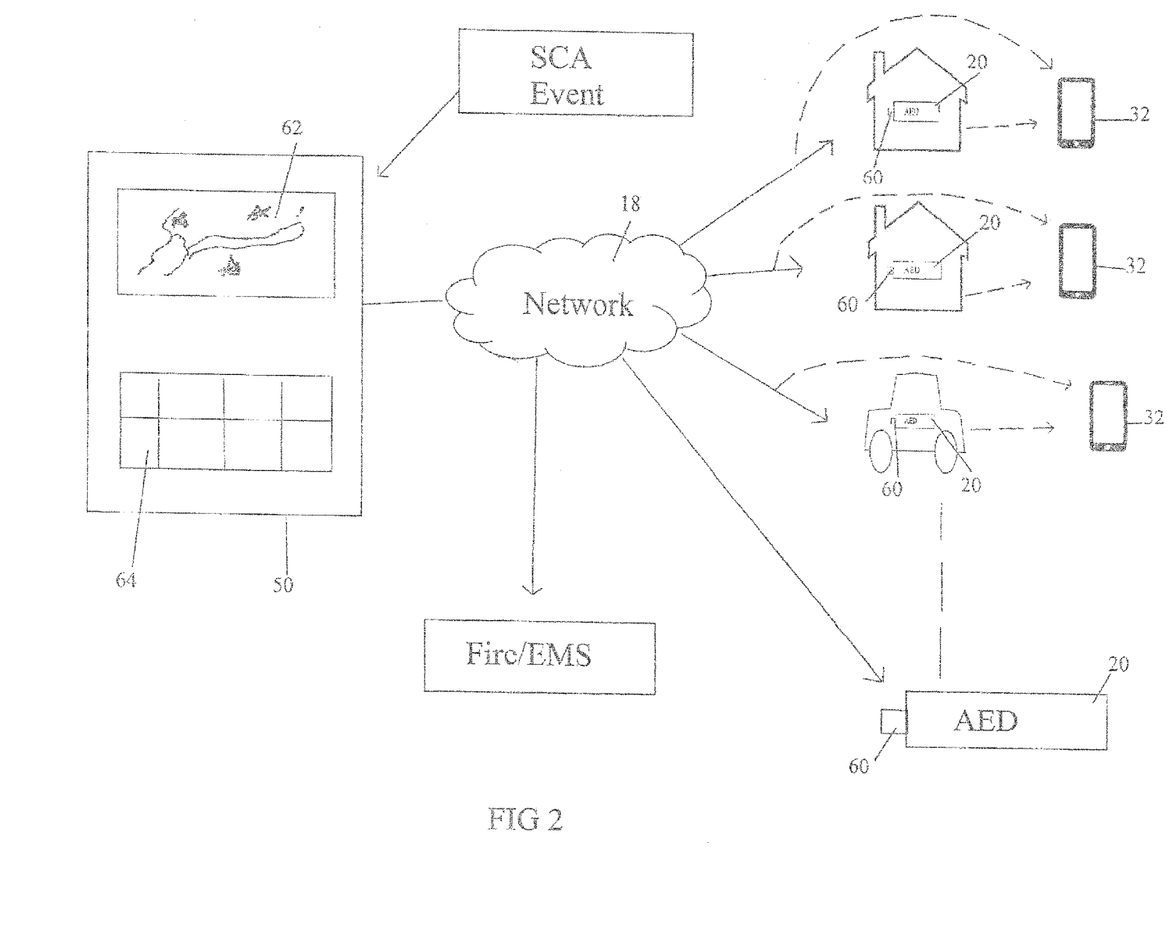
FIG. 2 is a diagrammatical illustration of the system of network-enabled automatic electronic defibrillators, in accordance with the first exemplary embodiment of the present disclosure.
Figure 3:
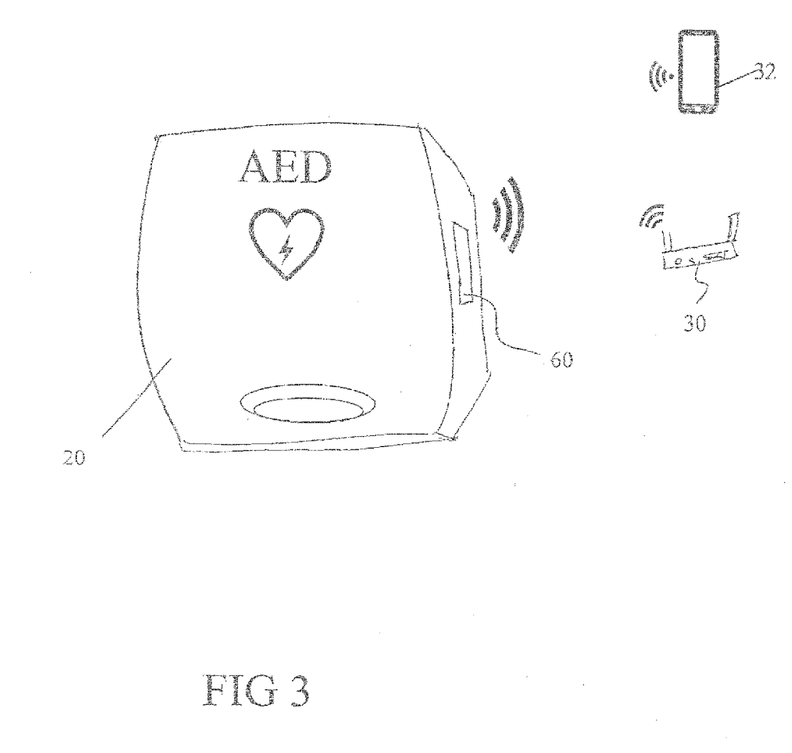
FIG. 3 is a diagrammatical illustration of an AED with a geographical-locating device, in accordance with the first exemplary embodiment of the present disclosure.

FIG. 2 is a diagrammatical illustration of the system of network-enabled automatic electronic defibrillators 10, in accordance with the first exemplary embodiment of the present disclosure. FIG. 3 is a diagrammatical illustration of an AED with a geographical-locating device, in accordance with the first exemplary embodiment of the present disclosure. As shown in FIG. 2, a plurality of AEDs 20 are connected to a network 18 which is connected to the controller 50. Each of the plurality of AEDs 20 may reside in or near a particular setting, such as a house or building, a car or other vehicle, and/or carried by a person. Each AED 20 may have a geographical-locating device 60 connected thereto which enables the controller 50 to determine a location of the AEDs 20.

The geographical-locating device 60 may be, for example, an RFID chip, a GPS chip, a NFC chip, or another known locating device. The geographical-locating device 60 may also be in communication with a cell phone 32, a router 30 of a local area network (LAN), or other communication device of an individual who is near the AED 20 or has access to it. The use of the geographical-locating device 60 on each AED 20 may be important to successfully using the system 10. It is necessary to know the location of the AEDs 20 at any given time, including when the AED 20 is needed in an emergency and when AEDs 20 are standing by in non-emergency situations. In one example, each AED 20 may have an active RFID chip attached so it can periodically register its location. Typically, AEDs are not moved, other than when used. Therefore, periodic location transmissions, e.g., hourly, may be sufficient, and can save energy, particularly, when running on battery power. The location may be provided by a MAC address or an identifier string associated with a residential LAN or other network through which the AED 20 is communicating.

The geographical-locating device 60 may be registered and accessible via WiFi at a unique WiFi residence. It is possible for the controller to ping (transmit a short message) to any number of AED 20 devices deployed to show all responding points on a map 62 of the controller 50, with each geographical-locating device 60 showing up as a locator node on the map 62. Other features, such as a control panel 64 may also be provided in the controller 50 to assist with identifying a location of an AED. Thus, it may be easy to show the location of the inventory of AEDs. Further, it is possible to identify the location using only short messages using very low bandwidth, no API, and no computing. Each geographical-locating device 60 may only need to be locatable or not on a map display 62 of the controller 60, but it is also possible for the location of the AED 20 to also be visible at other places, such as on the cell phones 32 of nearby individuals.

When a SCA event occurs, the controller 50 may transmit a message through the network and to the AEDs 20. In one of many alternatives, the controller 50 may transmit a message through the network and directly to the cell phone 32 or other communication device of a human individual who can assist with the AED 20 usage. Upon receipt of the message, the AED 20 and/or the cell phone 32 or other communication device may sound an alarm or provide another alert to indicate the need for the AED 20 to be used. The alarm or alert may include additional information about the situation, such as the location of the patient suffering from the SCA, contact information of the patient or another party assisting with the SCA, instructions on how to navigate to the location of the patient, information about other, nearby AEDs which have also been requested to assist with the patient, and other information that may be used to help with the emergency.

To assist with achieving the goals of the subject disclosure, it is desirable for manufactures of AEDs to make their devices more affordable, more portable, and less intimidating to use. As taught within the system 10, the AED may connect via Bluetooth, wireless, or other means to enable them to be located. Additionally, it is possible to use the same communication networks to achieve other tasks relative to the AEDs, such as monitor a battery status and to send alerts when they are activated. This can be accomplished by the manufacturers or by attaching RFID or other add-ons to them.

To help achieve the goal of the subject disclosure, home broadband, security, and medical monitoring services can put in place the ability to connect to AEDs and communicate with the devices and their users. An emergency call center staffed with trained medical personnel should automatically be connected to lead users through the steps to ensure that AEDs are used promptly and correctly when warranted. When an AED is activated, alerts will automatically be transmitted to emergency service providers such as ambulance services or fire departments. Alerts also should be enabled for family, friends, and neighbors.

Wireless networks should be prepared to play a similar role, particularly in the unlikely case that broadband service is not available. AEDs should connect via Bluetooth or wireless to smartphones. The smartphones can have applications that can also recognize the activation of an AED, contact emergency call centers and emergency services and guide users through the steps involved in ensuring successful use of the device. It is also possible that AEDs could be bundled into home broadband or security and medical monitoring services, for example, and leased much in the same way that broadband providers now lease modems to their subscribers. This option may be more attractive to consumers than outright purchase of a device.

Application developers readily can produce software for smartphones with the functionality described above. They should be able to interact with AEDs, connect users to emergency services, and provide guidance to AED users in emergency situations. These applications are important to the system 10 architecture. It is also envisioned that the system 10 architecture can be made mobile and extended to medical service providers like MDs, RNs, and medical students; public servants like policemen, security guards, park rangers; public transportation vehicles like taxis and postal trucks and many more. Also, $3^{rd}$ party groups and organizations such as home security networks, homeowner associations, condo complexes, and hotels are a market for these devices. Accordingly, with a call from the management of a large home owners association due to an emergency that requires an AED, the up-to-date closest residences with AEDs or other medical kits can be readily identified and summoned by a software driven text message if they are within a close distance of the patient in need of the AED. Overall, the community in which the system 10 is used will end up being safer due to the ability to harness the benefit of volunteer citizens who have opted to participate and lend medical assistance when needed. A similar concept could be applied to any other community, such as office buildings, malls, theme parks, etc.

It is further noted that the same system architecture can extend to other medical emergencies beyond those involving an AED. For example, nearby assistance can be requested for emergencies involving snake bite, acute asthma, anaphylactic shock, chest pains, etc., by contacting individuals who may be able to assist.

Additionally, it is noted that geographical-locating device 60 discussed herein also may be adapted to be a sensor by providing a button to send an alert message of a suspected cardiac incident. In this way, the AED on which the geographical-locating device 60 is connected becomes a means of communication which requires very low bandwidth and essentially no computing power. In a similar aspect, the geographical-locating device 60 may be associated with other sensors relating to heart health, such as wearable sensors of heart rate or heart rhythm, and relay health information to the controller 50 or a medical monitoring service when a medical emergency is suspected, i.e. if data is beyond a normal threshold. It is further possible for the geographical-locating device 60 to be mobile and used in cars, public transportation, watercraft, and other vehicles. For example, the geographical-locating device 60 may be outfitted with connectivity to car onboard diagnostic (OBD) port so it is possible to track the location of the AED 20 as it changes locations. In another example, if a person with an AED 20 leaves home and brings the AED in a car, it is possible to track the AED 20 as a mobile trackable asset. Furthermore, it is possible to integrate the geographical-locating device 60 with an AED 20 via an API by a manufacture of the AED at a design stage, or it may be possible to retrofit existing AEDs 20 with a geographical-locating device 60.

Figure 4:
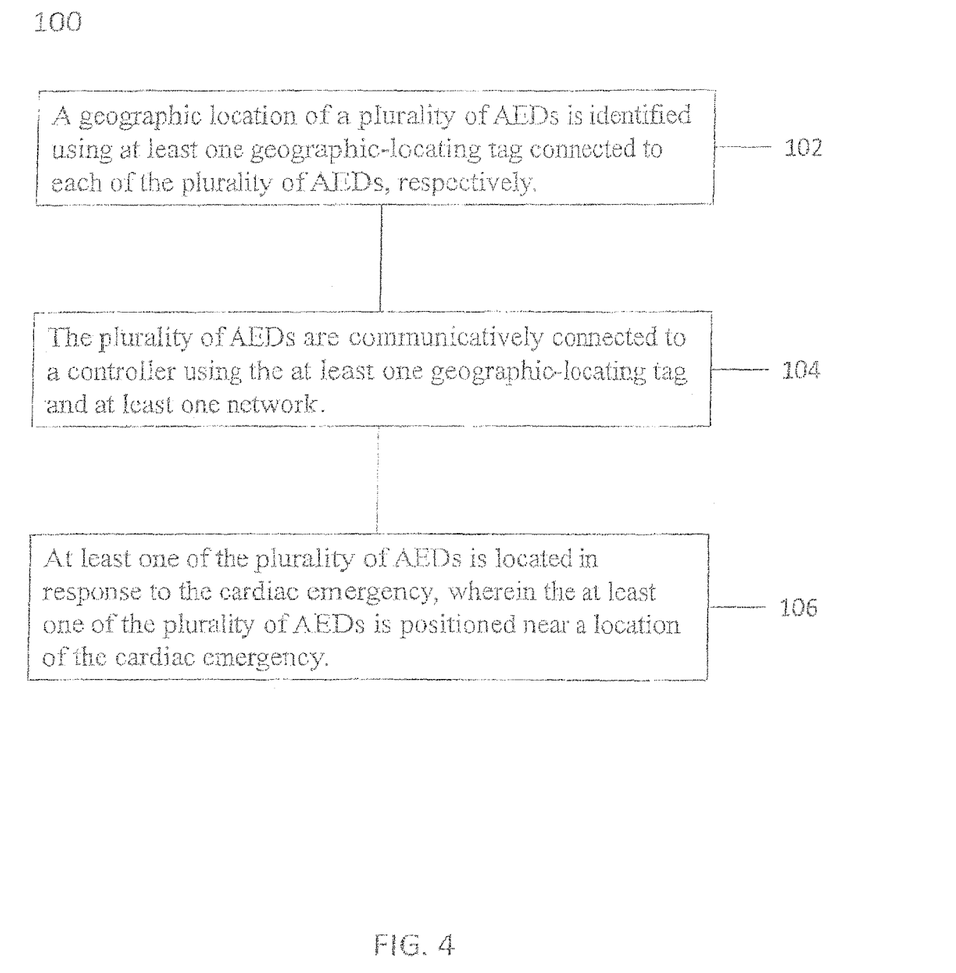
FIG. 4 is a flowchart illustrating a method of locating an AED for use in a cardiac emergency, in accordance with the first exemplary embodiment of the disclosure.

FIG. 4 is a flowchart 100 illustrating a method of locating an AED for use in a cardiac emergency, in accordance with the first exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 102, a geographic location of a plurality of AEDs is identified using at least one geographic-locating tag connected to each of the plurality of AEDs, respectively. The plurality of AEDs are communicatively connected to a controller using the at least one geographic-locating tag and at least one network (block 104). At least one of the plurality of AEDs is located in response to the cardiac emergency, wherein the at least one of the plurality of AEDs is positioned near a location of the cardiac emergency (block 106).

The system may further include any number of additional steps, functions, or variations. For example, the at least one geographic-locating tag further comprises at least one of: a RFID chip, a GPS chip, and a NFC chip, and the at least one network connection may further comprises at least one of: a wireless network, a hardwired network, a WiFi network, and a Bluetooth network. The use of the at least one of the plurality of AEDs may be requested with an electronic message to assist with the cardiac emergency. The geographic location of the plurality of AEDs may be identified based on a network identification of the network, wherein the network identification further comprises at least one of: a MAC address, an identifier string, a WiFi network ID, and a cellular network. A graphical display having a map may be used to display the identified geographic location of the plurality of AEDs. Further, it may be desirable to communicate with a human individual associated with at least one of the plurality of AEDs with a text message transmitted to portable electronic communication device of the human individual. Additional communication may include messages transmitted between the controller and the location-providing tag of each of the plurality of AEDs, such as by transmitting a status ping at predetermined intervals, wherein the status ping identifies at least one of a functioning state and geographic location of the plurality of AEDs, by transmitting a changed location status ping when a geographic location of the plurality of AEDs is changed, by transmitting an alert message having a notification of a medical emergency to a human individual associated with one or more of the plurality of AEDs, and/or by transmitting an alert message having a notification of a medical emergency to a medical care provider.

Various changes may be made in the above invention without departing from the spirit and scope thereof. For example, rather than physically tagging the AED's, the location of the AED's may be "electronically" tagged by mapping. Also, it is not necessary to pinpoint the location of the AEDs. Rather, it is sufficient to communicate with a human individual in the house hold associated with the AED.

Still other modifications are contemplated. For example, referring to FIG. 5, in another embodiment of the present disclosure, AEDs 120 are located in selected homes 122 of trained volunteers. Homes 122 are scattered through a neighborhood 124 essentially to provide geographic coverage of the entire neighborhood. As used herein "homes" may be detached homes, common wall homes, apartments, etc.

Figure 5:
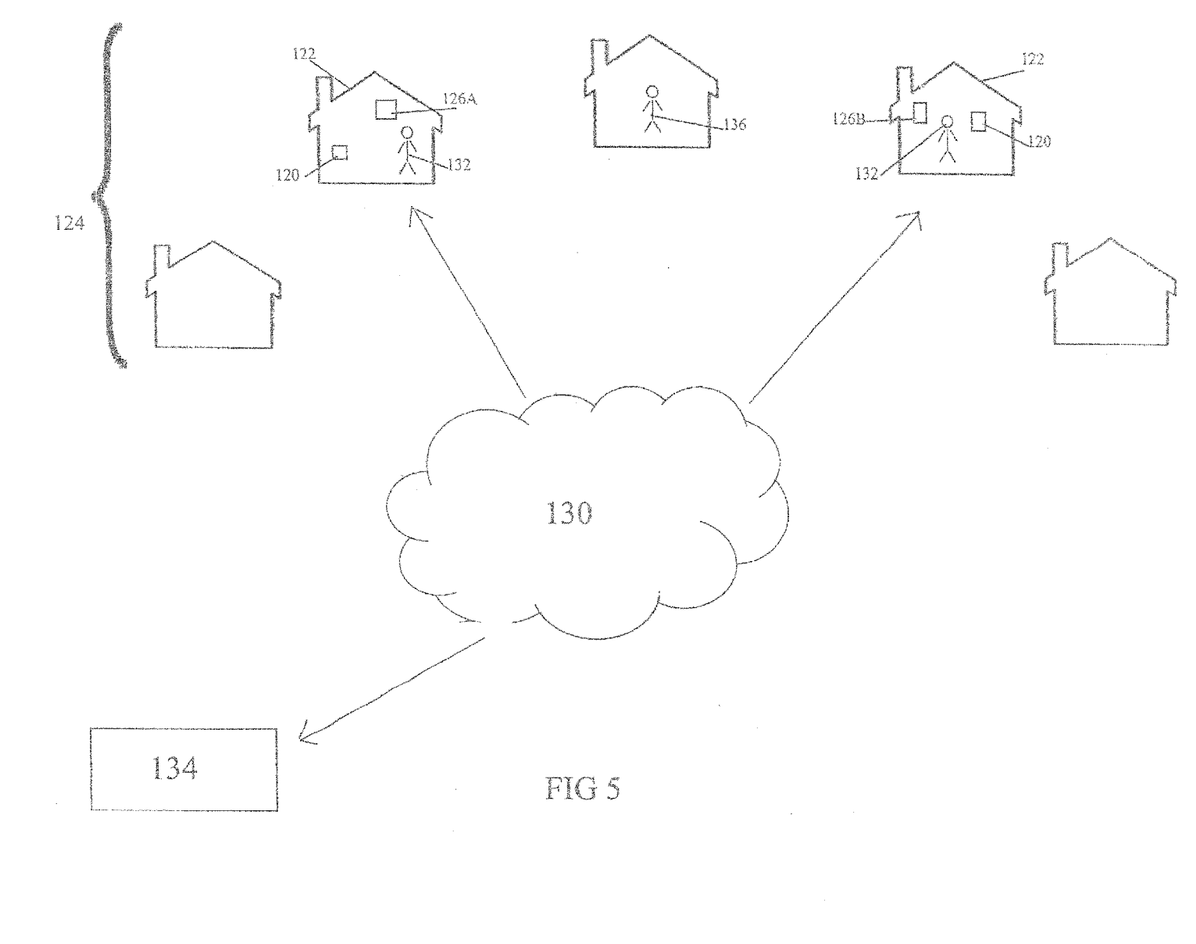
FIG. 5 is a diagrammatical illustration of a network of AEDs located in homes of volunteers in accordance with a second embodiment of the present invention.

In this scenario, each volunteer agrees to monitor the AED's readiness (battery status, etc.) and, if they are home, to respond to cardiac emergencies in their neighborhood. Volunteers are alerted to cardiac emergencies via text messages to their smart phones 126A or dedicated receivers 126B sent by central emergency dispatcher 128, typically a 911 call center. In practice, an emergency call made to a 911 call center will be screened by a 911 operator 130, and if coded as a possible sudden cardiac arrest (SCA), trigger messages to nearby emergency personnel, i.e., an EMS team 134, and simultaneously or shortly thereafter, i.e., within a minute or less, send messages to local volunteers 132. Signals would include the address where the SCA victim is located. Inasmuch as the neighborhood volunteers 132 typically will be located closer to the site of the SCA victim 136, it is expected the local volunteers 132 will reach the SCA victim 136 sooner than the EMS team 134, and begin treatment. Once the EMS team 134 reaches the SCA victim 136, the volunteer can then hand off the care to the EMS team. Under normal circumstances, it is expected the volunteers will reach the SCA victim ahead of the EMS team, thereby increasing the possibility of a timely response, and survival.

Figure 6:
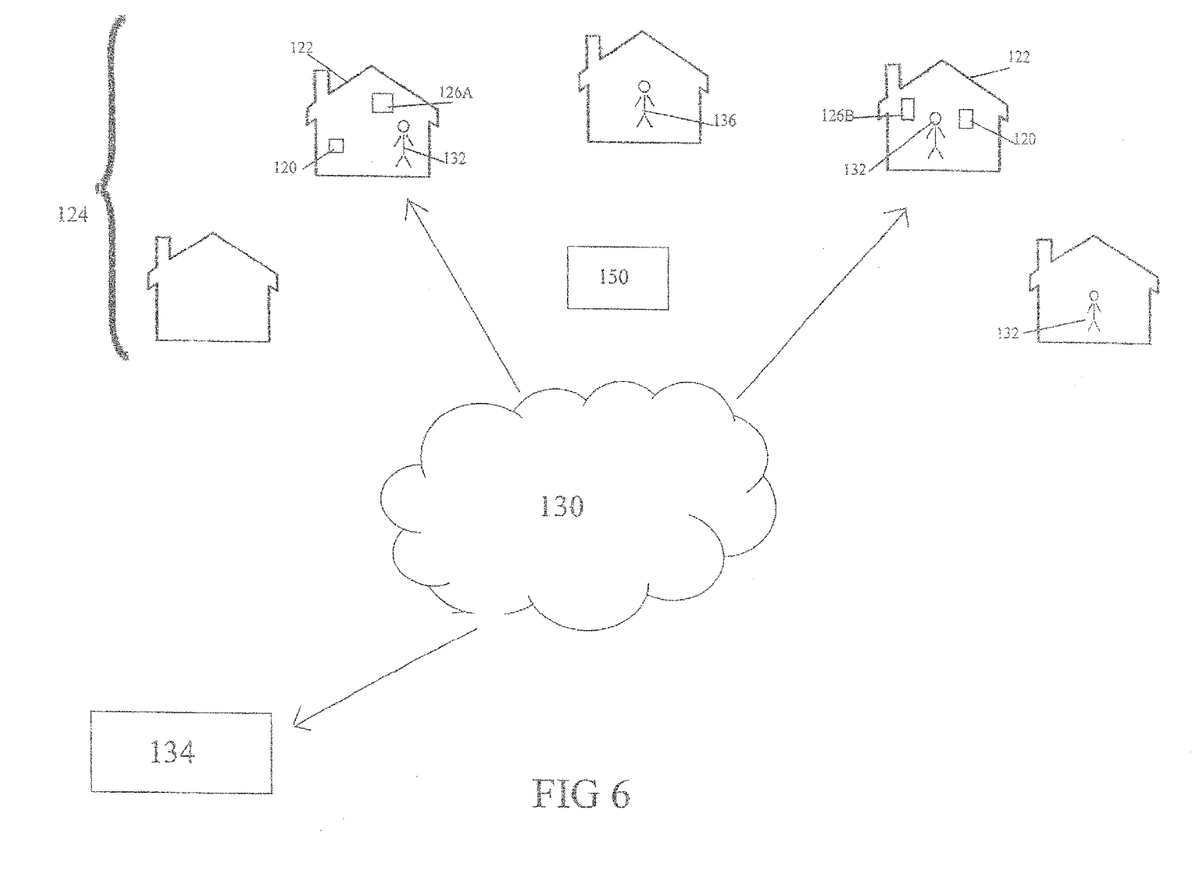
FIG. 6 is a diagrammatic view similar to FIG. 5, of a residential neighborhood in which AEDs are located in public areas.

Referring to FIG. 6, rather than locate AEDs 120 within households, or in addition to locating AED's within households, the AEDs 120 also could be scattered around communities in secure outdoor lockboxes 150. In such case, when an emergency occurs, the 911 operator would communicate not only with trained volunteers 132 in the neighborhood, but also send a signal 152 to temporarily unlock the lockboxes 150 giving the trained volunteers 132 time to fetch the AED 120 and rush the AED to the SCA victim. As a practical matter, the lockbox 150 would need to be left unlocked for just a few minutes, e.g., five to eight minutes unless the AED 120 was removed. However, if the AED 120 is removed, the lockbox 150 may remain unlocked until the AED 120 is returned, whereupon the lockbox 150 may automatically relock by sensing the return of the AED, e.g., by a barcode reader or the like. Alternatively, volunteers may be provided with keys or dongles or the like for unlocking the lockboxes. The lockbox may be triggered to relock either by a signal from the 911 call center, or by a volunteer returning the AED to the lock box.

In the case of the lockbox embodiment, the lockbox preferably may include one or more solar cells 152 for charging an internal battery 154 for a communication device 156 and also to power an electronic lock 158. Lockbox 150 also may include heating and/or cooling devices 160 for maintaining the interior of the lockbox 150 within a temperature range for optimal performance of the AED 120.

Figure 7:
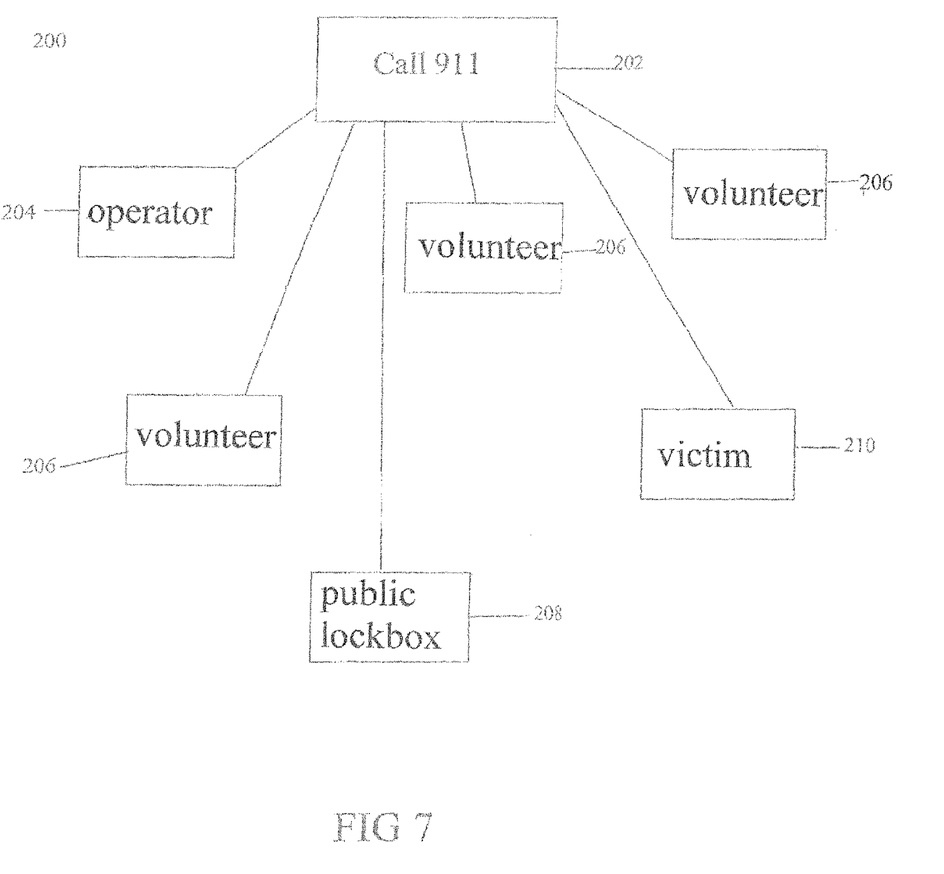
FIG. 7 is a flow chart illustrating a method of using an AED in accordance in a cardiac emergency, in accordance with a second embodiment of the disclosure.

FIG. 7 is a flowchart 200 illustrating a method of alerting trained operators with automatic electronic defibrillators to a cardiac emergency in accordance with another exemplary embodiment of the disclosure. It should be noted that any process descriptions or blocks in flowcharts should be understood as representing modules, segments, portions of code, or steps that include one or more instructions for implementing specific logical functions in the process, and alternative implementations are included within the scope of the present disclosure in which functions may be executed out of order from that shown or discussed, including substantially concurrently or in reverse order, depending on the functionality involved, as will be understood by those reasonably skilled in the art of the present disclosure. As shown by block 202, an emergency call is made to 911. If the 91 operator determines the emergency to be a cardiac event, the 911 operator sends an alert to 911 operator (block 204) advising the location of the victim. Simultaneously, or shortly thereafter, the 911 operator sends a similar alert to neighborhood volunteers block 206 advising the neighborhood volunteers of the cardiac event and the location of the victim. Also, in the case of a community in which AEDs are scattered in public lock boxes, a signal is sent to the lock boxes (block 208) unlocking the lock box, and also providing an address of the victim. At the same time, other trained volunteers also may be alerted of the cardiac event and the address of the victim (block 210). Such volunteers may pick up an AED at the public lock box 208, and from there rush to the victim to assist until the EMS team arrives.

Still other changes are possible. Accordingly, as used herein, and in the following claims, the term "location-providing tag positioned on or connected to each of the AEDs" is intended to include both a physical tag on or associated with the AED, an electronic app or map showing the location of the AED, or a cell phone or other communication device associated with a person or persons living in a home where the AED is physically located.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. An emergency response system for alerting trained neighborhood volunteer operators to collect an automatic external defibrillator (AED) and deliver the AED to a neighborhood cardiac emergency, comprising:
    at least two AEDs held in lockboxes in different geographic locations in a neighborhood community;
    a central emergency dispatch hub configured to send an emergency alert to the trained neighborhood volunteer operators; and
    a device configured to communicate with the trained neighborhood volunteer operators and alert the trained neighborhood volunteer operators of the neighborhood cardiac emergency and a location of a victim of the neighborhood cardiac emergency,
    wherein the lockboxes are configured to unlock automatically upon receiving a signal from the central emergency dispatch hub or from a trained neighborhood volunteer operator in a vicinity of the lockbox and to remain unlocked for a period of time after receiving a signal and then relock automatically or remain unlocked if an AED is removed and relock automatically only after the AED is returned to the lockbox.

2. The system of claim 1, wherein the central emergency dispatch hub is configured to communicate to the trained neighborhood volunteer operators via a smart phone or dedicated receiver.

3. The system of claim 1, wherein the lockboxes include one or more solar cells.

4. The system of claim 3, wherein the lockboxes each include a heater and/or cooler for heating or cooling the interior of the lockbox.

5. The system of claim 1, wherein the central emergency dispatch hub is configured to simultaneously communicate with the trained neighborhood volunteer operators and an EMS team.

6. The system of claim 1, wherein additional AED's also are located in residences of one or more of the trained neighborhood volunteer operators.

7. A method for improving response time for dispatching AED's with trained neighborhood volunteer operators to a victim of a neighborhood cardiac emergency, comprising, providing an emergency response system as claimed in 1, and alerting the trained neighborhood volunteer operators of a cardiac event and the location of the victim.

8. The method of claim 7, wherein the trained neighborhood volunteer operators are alerted via a network selected from a wireless network, a hardwired network and a WiFi network.

9. The method of claim 7, wherein the trained neighborhood volunteer operators are alerted via a smart phone.

10. The method of claim 7, wherein the trained neighborhood volunteer operators are alerted at the same time or shortly thereafter the central emergency dispatch hub alerts an EMS team.

* * * * *